(12) United States Patent
Hulten et al.

(10) Patent No.: US 6,187,749 B1
(45) Date of Patent: Feb. 13, 2001

(54) METHODS FOR VARIATION OF CHROMATIN CONDENSATION

(75) Inventors: Maj Hulten; Subhasis Banerjee, both of Birmingham (GB)

(73) Assignee: Simeg Ltd., Moseley (GB)

( * ) Notice: Under 35 U.S.C. 154(b), the term of this patent shall be extended for 0 days.

(21) Appl. No.: 08/693,198

(22) PCT Filed: Feb. 10, 1995

(86) PCT No.: PCT/GB95/00264

§ 371 Date: Dec. 10, 1996

§ 102(e) Date: Dec. 10, 1996

(87) PCT Pub. No.: WO95/21860

PCT Pub. Date: Aug. 17, 1995

(Under 37 CFR 1.47)

(30) Foreign Application Priority Data

Feb. 10, 1994 (GB) .................................. 9402586

(51) Int. Cl.⁷ ............................ A61K 38/17; C07K 14/46
(52) U.S. Cl. ............................................. 514/12; 530/350
(58) Field of Search ............................... 530/350; 514/12

(56) References Cited

PUBLICATIONS

Banerjee, S., et al. (1994) Mol. Reprod. and Devel. 37, 305–317.*
Cheng, X., et. al. (1993) Cancer Res. 53, 5592–5596.*
Wood, E. R., et. al. (1990) J. Cell Biol. 111, 2839–2850.*
Adachi, Y., et. al. (1991) Cell 64, 137–148.*
Adlakha, R. C., et. al. (1984) J. Cell Sci. 65, 279–295.*
Maleszeski, M. (1990) Mol. Reprod. and Devel. 27, 244–248.*

* cited by examiner

*Primary Examiner*—Charles L. Patterson, Jr.
(74) *Attorney, Agent, or Firm*—Larson & Taylor PLC (57) ABSTRACT

The present invention relates to methods for decondensation and/or condensation of chromatin or chromosomes through the addition of substances to condensed or decondensed chromatin or chromosomes respectively. In particular, the invention relates to a method for decondensing and subsequently optionally recondensing chromatin in cells at the interphase stage of the cell cycle and to a method for condensing chromatin or chromosomes following disruption of sperm. The present invention also relates to substances for the decondensation and/or condensation of chromatin or chromosomes and to kits comprising said substances, as well as to the use of these substances in chromatin or chromosome analysis, reproduction in particular fertility assessment, the diagnosis and treatment of infertility, assisted conception either in the clinic or naturally and contraception. A particular factor identified is a decondensation factor which has a molecular weight of 20 kDa and which is obtainable from HeLa cells.

13 Claims, 4 Drawing Sheets

Fig.4. PURIFICATION SCHEME FOR CHROMATIN DECONDENSATION FACTOR

METHODS FOR VARIATION OF CHROMATIN CONDENSATION

The present invention relates to methods for decondensation and/or condensation of chromatin or chromosomes through the addition of substances to condensed or decondensed chromatin/chromosomes respectively. In particular, the invention relates to a method for decondensing and subsequently optionally recondensing chromatin in cells at the interphase stage of the cell cycle and to a method for condensing chromatin/chromosomes following disruption of sperm. The present invention also relates to substances for the decondensation and/or condensation of chromatin/chromosomes and to kits comprising said substances, as well as to the use of these substances in chromatin/chromosome analysis, reproduction in particular fertility assessment, the diagnosis and treatment of infertility, assisted conception either in the clinic or naturally and contraception.

Chromatin is a DNA protein substance of which chromosomes are made. The expression 'chromatin/chromosome' used herein means that both terms can be applied.

The analysis of chromatin/chromosomes is of fundamental importance in assessing the genetic well-being of an organism. In man, analysis of chromosomes is undertaken routinely on foetal cells isolated, for example, by amniocentesis and this allows the prenatal diagnosis of such disabling genetic diseases as Down Syndrome usually caused by the presence of an extra copy of chromosome 21. In several cases, the peripheral blood cells are analysed in relation to the suspected presence of a genetic disease in the individual. For many cancers, chromosomes are analysed in order to identify abnormalities which either correlate with the occurrence of a particular tumour type or which predict the subsequent rate of progression of the cancer and thus the well-being of the patient. In addition to these routine analyses of chromosomes, there has arisen in recent years a desire to undertake the same type of chromosome analysis on human sperm especially with suggestions that exposure to ionising radiation and chemicals acting in the same way as ionising radiation (so-called radiomimetic agents) might lead to inheritable chromosome defects in the germ-line.

Despite these examples of the analysis of chromosomes undertaken at present, it is clear that the more widespread analysis of chromatin/chromosomes in medical diagnosis is limited by the technical difficulties of undertaking such a analyses. Chromatin/chromosomes undertake changes in gross structure during cell division whereby chromatin/chromosomes at the metaphase (mitotic phase) of the cell cycle are condensed and usually readily visible upon cell lysis with hypotonic solutions but whereby at the interphase stages of the cell cycle, the chromatin/chromosomes are decondensed and not readily visible upon cell lysis. Chromatin/chromosome analysis most often relies upon culture of cells in vitro to accumulate actively dividing cells with condensed chromosomes in the metaphase stage of the cell cycle. The in vitro cell culture required may take days or weeks to accomplish, and some cells, especially those which are "terminally" differentiated such as nerve cells or sperm cells, are not at all amenable to cell culture in vitro.

As even in actively dividing cell populations, metaphase cells are rare, several methods have been developed to allow analysis of chromosomes in mammalian cell preparations. Commonly, dividing cells are treated with chemicals such as colchicine and vincristine which block dividing mammalian cells in metaphase producing an increased number of cells with condensed visible chromosomes.

More recently, fluorescently-labelled nucleic acid probes specific for the centromeric regions of individual chromosomes have been used to detect chromatin/chromosomes directly in interphase cells whereby fluorescent probes hybridise to very small segments of the decondensed chromatin/chromosomes in order to produce a well defined fluorescent spot indicating the presence of a chromosome.

Both of these widely used methods have drawbacks. Metaphase inhibitors rely on actively growing cell populations to be effective and many cell samples isolated from blood or tissues are usually slowly growing thus precluding an abundance of cells trapped in metaphase. Whilst fluorescent probes which recognise small regions on individual chromatin/chromosomes can give well defined fluorescent spots on interphase cells, probes which recognise a larger region such as a whole chromosome or large fragment of chromatin/chromosome may give rise to a diffuse fluorescent smear which may preclude, for example, the counting of individual chromatin/chromosomes or chromatin/chromosome fragments recognised by the probes. The use of nucleic acid probes can present another problem in relation to chromatin/chromosome decondensation whereby, in order for a nucleic acid probe to hybridise to a chromatin/chromosome, the DNA in the chromatin/chromosome has to be denatured, a process which itself can disrupt the structure of the chromatin/chromosome to make identification by the probe difficult.

A further technique which is applicable in certain circumstances is known as premature chromosome condensation (PCC). It was first described by Hittelman and Rao, (1978) Cancer Res. 38:416–423. This technique results in the condensation of chromatin/chromasomes in interphase cells. It may be achieved in vitro using CHO or HeLa cells, or inactivated Sendai virus. Alternatively non-physiological agents such as polyethylene glycol (PEG) may be involved as well as synthetic acidic proteins such as poly L-glutamic acid and extracts from non-mammalian cells such as Xenopus egg extracts from germ-line cells such as hamster oocytes. The technique has been utilised many times in the art, for example in studies of acute lymphblastic leukaemia (Macleod et al., Genes, Chromosomes & Cancer, (1989) 1, 135–138). It is however a very difficult technique to apply in the laboratory and only a limited number of research groups utilise it.

For sperm cells, current techniques for genetic analysis are difficult. This is because of the unusually tight compactment of nucleic acids in sperm heads thus precluding analysis. Often the microinjection of individual sperm into hamster eggs in order to achieve visible chromosomes from human sperm cells is required ("pseudofertilisation"). This is a peculiarly difficult technique to operate and only a few research groups undertake it. Another technique utilised is fluorescence in situ hybridisation (FISH) which employs fluorescently-labelled nucleic acid probes specific for the centromeric region of the chromosome as discussed above. The application of this technique is described by for example Hultén and Goldman in Chromosomal Alterations ed. obe and Natarajan (1994), Springer-Verlag.

A number of in vitro systems, which mimic the events at fertilisation, have been developed in order to enable the changes in chromatin structure and the mechanisms of chromatin remodelling to be studied. These are reviewed by Leno et al.,in John Innes Review, The Chromosome, Ed. J S Heslop-Harrison, (1992) R. B Flavell Bros. Scientific Publishers. p135–147. The principal component found to be effective in the decondensation and remodelling of sperm is nucleoplasmin, a protein isolated from the eggs of *Xenopus laevis*.

For many cell types, such as foetal cells in amniotic fluid, the quality of chromosome preparation is highly variable between different samples even after several weeks of in vitro cell culture. Precise identification of chromosomes is often undertaken by "banding" whereby chromosomes stained with various dyes show a characteristic banding pattern across the length of the chromosome. This is particularly important in identifying fragments of chromosomes which have translocated onto another chromosome and also in scoring less gross lesions in chromosomes such as small deletions of chromosome material which might have little visible effect on chromosome length but which might result in the visible loss of a stained band. Critical in the achievement of a good interpretable banding pattern is the generation of optimally compact and condensed chromosomes. For all of these applications and many others, there is a need for technology which can actively generate adequately condensed chromosomes which can be easily enumerated, easily detected even with nucleic acid probes for whole chromosomes and which can be successfully "banded".

The applicant has found that polypeptides present in human somatic cells are effective in chromatin/chromosome decondensation and recondensation, and in particular in the decondensation, remodelling and recondensation of sperm nuclei. In other words, a number of physiological functions of the human egg can be mimicked in cell-free extracts obtained from somatic cells cultured in vitro. The applicant has found that factors and protein components, which mimic physiological activities of the human egg are present in somatic cells. These components can be chromatographically purified to homogeneity from the cell-free extracts and their roles in sperm chromatin/chromosome decondensation and condensation can be established and utilised.

In a preferred embodiment of this invention, the components present in the somatic cell-free extracts can induce sperm nuclear dispersion very rapidly (within 5 min) and chromatin/chromosome remodelling within an hour. When these transformed nuclei are subjected to chromosome condensing environment by adding another cell-free extract prepared from highly synchronised mitotic cells, chromatin/chromosome-like structures are visible within one hour. The factors or polypeptides giving rise to the decondensation effects may be isolated from interphase cell-free extracts using conventional techniques as exemplified herein which can facilitate effective and quantitative sperm nuclear dispersion.

Thus in a first aspect, the present invention provides a polypeptide obtainable from somatic cells which is capable of effecting decondensation of chromatin/chromosomes, for example the decondensation of sperm chromatin. Suitably the polypeptide is obtainable from human somatic cells, such as HeLa cells, and in particular from interphase cells A suitable polypeptide having a molecular weight of 20 KDa has been identified in human HeLa cell extract.

The above-mentioned polypeptides act as decondensation factors. Decondensation of sperm chromatin is crucial in the fertilisation process. Under physiological conditions, the sperm nucleus undergoes a series of changes following its entry into an egg, such as sperm nuclear envelope breakdown, chromatin decondensation, chromatin remodelling by the removal of basic protamines and simultaneous assimilation of egg-specific chromosomal proteins, and recondensation of dispersed chromatin.

The reaction of sperm nuclei to decondensation factors in the egg is probably a factor in determining fertility. If the sperm is incapable of decondensing appropriately in the presence of such factors, infertility or reduced fertility may result. It is also likely that the timing of the contact between the sperm and the decondensation factor is important. Exposure of sperm to effective amounts of decondensation factor prior to fertilisation may render them incapable of pushing through the membrane of the egg and the fertilisation will fail. Hence a decondensation factor of this kind has widespread application in the field of reproduction such as fertility assessment, diagnosis of sub-fertility and infertility treatment as well as in contraception.

In addition, the response of the sperm nuclei to decondensation factors is believed to be related to other sperm parameters such as viability and motility which are indicative of their general health and functional capacity. Thus the quality of the sperm may be assessed on the basis of the reaction to decondensation factors.

In particular the invention provides a method for testing the fertility or quality of sperm which method comprises contacting a sample of sperm nuclei with a chromatin decondensation factor and assessing whether decondensation of the chromatin occurs. Suitable chromatin decondensation factors for use in this method include extracts from somatic cells, particularly interphase somatic cells as described above, a decondensation effective polypeptides obtainable therefrom.

Preferably the sperm nuclei are first permeabilized for example by contacting them with a permeabilizing agent such as lysolecithin. This has the effect of ensuring the the decondensation factor reaches the chromatin.

The methods may be carried out in a laboratory wherein sperm nuclei may be formed as smear samples on a slide and assessed visually under a microscope to determine the extent of decondensation. The samples may be subjected to the usual visualisation techniques such as the application of chromatin/chromosome dyes or fluorescent labels in order to assist in the visual assessment in a conventional manner.

Alternatively, the test may be based upon immunoassay techniques, whereby a sperm sample is subjected to the decondensation factor in a form suitable to effect sperm chromatin decondensation, and thereafter, decondensed sperm chromatin is detected using for example a labelled specific binding partner such as an antibody which binds to decondensed sperm chromatin and which generates a visual signal. The state of DNA methylation and/or DNA states which differs in decondensed chromatin/chromosomes from that of condensed chromosomes as is well known in the art may provide the basis for detecting decondensed chromatin/chromosomes. Generally the intensity of the colour signal produced by the reagent which detects the decondensed chromatin/chromosomes will be proportional to the quality of the sperm, but other systems may be envisaged.

Such a test may be formed as a rapid assay test for general use. Examples of such labels include gold and latex labelling means as is conventional in the art. The test may be arranged in a kit form, for example a dipstick type kit form. However, other arrangements of the kit will be apparent to the skilled person and fall within the ambit of the invention.

Thus the invention provides a kit for testing the fertility or quality of a sperm sample which comprises a chromatin decondensation agent for sperm, combined with reagents able to detect the presence of decondensed sperm chromatin/chromosomes.

These kits and testing methods may be employed in the analysis of reproductive systems. These systems include both animal and plant systems. They may be utilised in the field of human fertility, animal husbandry and plant breeding. For example, in the breeding of animals such as cattle, sheep, horses, dogs and other domestic or captive mammals, identification of males which are particularly fertile is advantageous, whereas males whose sperm is of less good quality may be avoided in breeding processes.

In view of the mode of action of the decondensation factors of the invention, they may also find utility in the treatment of infertility, for example, in that which is due to an inappropriate reaction of sperm nuclei to decondensation factor(s) present in the egg.

In such a case the invention provides a method which comprises contacting a sperm cell with a decondensation factor and thereafter injecting said sperm cell into the cytoplasm of the egg in vitro, and other forms of assisted conception including their enhancement of natural conception.

Infertility could be due to the presence of inappropriate amounts of natural decondensation factor produced in the egg and/or the production of appropriate amounts at the wrong time. In such a case, fertility treatment may require administration of an agent which regulates the release of the natural decondensation factor. Examples of such agents may comprise specific binding partners such as antibodies or receptors for the protein or chemical inhibitors of the protein which may be applied for example in the form of pessaries. Such blocking agents, which form a further aspect of the invention, can be derived for example using biochemical testing or assay methods, which are known or could be devised by the person skilled in the art.

Regulation of the release of natural decondensation factor in this way may be combined with other treatments which affect fertility, such as follicular stimulating hormone in order to manipulate the fertility and conception process.

As an aid to fertility and family planning, it is useful to assess the ovulation cycle of the female. As the production of decondensation and recondensation factors are expected to be crucial in the fertilisation process, it may be expected that the production of these factors is also cyclical. As the applicants have found that the factors is present in somatic cells, the possiblity of testing the ovulation pattern arises.

Thus the invention also provides a method for detecting the status of a female ovulation cycle which method comprises taking a physiological sample, such as blood or saliva, from said female and analysing the amount of sperm decondensation and/or recondensation factor present in said sample.

Test of this kind can utilise immunological techniques for analytical purposes. For instance, the presence of the relevant factor may be detected using a labelled binding moiety such as an antibody or antibody binding fragment which is specific for the relevant factor. Such a test may be supplied in kit form, for example a rapid assay kit form as is conventional in the art. Such kits form a further aspect of the invention.

For contraceptive purposes, "inactivation" of sperm prior to fertilisation is to be desired. The application of a decondensation factor at this time would be effective in this inactivation. Thus the invention also provides a spermicidal agent comprising a sperm decondensation factor such as somatic cell extract of a polypeptide extracted therefrom as described above, in combination with a carrier.

Such spermicidal agents may be in the form of vaginal gels, douches or pessaries or they may be incorporated into contraceptive devices such as condoms or cervical cap devices. Furthermore the invention provides a method of contraception which comprises applying to sperm or to the environs thereof, a chromatin decondensation factor.

Since both the decondensation and recondensation factors are essential for a successful fertilisation process, the removal or blocking of these in the female may provide a further means of contraception. Thus the invention further provides a method of contraception which comprises administering to a female a reagent which inhibits production of sperm decondensation or recondensation factor. Such reagents may act at the cDNA level, for example using anti-sense constructs to inhibit expression of one or both of these factors or at the protein level by means of for example antibodies or chemical agents.

In a preferred embodiment of this invention, there are provided substances from cells, for example mammalian cells, arrested in mitosis which can effect the condensation of chromatin/chromosomes in interphase cells and dissociated sperm nuclei. Such substances can either be provided as a crude mixture prepared by lysis of mitotic cells, such as mammalian cells, and precipitation of proteins or as purified protein factors responsible for chromatin/chromosome condensation. Thus in a second major aspect, the invention provides a polypeptide obtainable from somatic cells arrested in mitosis which is capable of effecting condensation of decondensed chromatin/chromosomes. Again suitably the somatic cells are human somatic cells, such as HeLa mitotic cells.

The polypeptide obtainable from metaphase cells acts as a condensation factor. Condensation factors of this sort may find application in chromatin/chromosome analysis, for example in genotoxicity studies, in order to overcome the problems associated with the presence of chromatin/chromosomes in decondensed form as discussed above as well as in reproduction, in combination with the above-mentioned decondensation factors in the treatment or diagnosis of infertility, or more generally.

An aspect of the invention is based on the observation that extracts from cell nuclei are effective in condensing dispersed chromatin/chromosomes and thus have the potential for permitting analysis of chromatin/chromosomes when dividing cells are not readily available. Thus many of the difficulties in analysis of chromatin/chromosomes can be solved by the condensation of dispersed interphase chromatin/chromosomes without intervening in vitro cell culture or where cell culture is not possible as with terminally differentiated cells.

In a further aspect the invention provides a method for the condensation of chromatin/chromosomes in vitro, which method comprises contacting said chromatin/chromosomes with a chromatin/chromosome condensation factor such as an extract from somatic cells arrested in mitosis or a polypeptide obtainable therefrom, which is capable of effecting condensation of decondensed chromatin/chromosomes. A further aspect of the invention relates to a kit for use in this method, which kit comprises an extract or a purified protein which effect the condensation of chromatin/chromosomes, other reagents as required for the analysis of chromatin/chromosomes and instructions for the condensation of chromatin/chromosomes.

Suitably the method may be applied to the condensation of mammalian chromatin/chromosomes.

The applicants have resolved some of the difficulties in analysis of human sperm chromatin/chromosomes by effecting an initial decondensation of sperm nuclei (as discussed above) and a subsequent condensation of sperm chromatin/chromosomes.

Thus the invention further provides a method for analysing or testing the fertility or quality of sperm which method comprises contacting a sample of sperm with:

(a) a chromatin/chromosome decondensation factor; and
(b) a condensation factor;

and observing whether acceptable decondensation, remodelling and condensation occurs.

In this method, the applicants have found that at least step (a) is effected in the presence of ATP and magnesium ion in order to assist remodelling.

As discussed above, the factors of the invention may be in the form of cell extracts or isolated polypeptides. One method for obtaining an isolated polypeptide in accordance with the invention comprises culturing a somatic cell, and isolating the polypeptide from cell extracts. Techniques used in the isolation are conventional in the art and include affinity chromatography.

Once isolated, a polypeptide may be utilised in order to raise antibodies in the usual way. The antibodies can be employed to screen a cDNA library for example a human cDNA library to identify the genes. Such antibodies and other binding moieties such as antibody fragments form a further aspect of the invention.

Once this has been done, isolated CDNA clones can be used for the production of the polypeptide. Alternatively the genes may be sequenced again using conventional techniques. The invention further provides a cDNA encoding a polypeptide of the invention.

This provides the possibility for generating polypeptide using recombinant means for example by forming a suitable replicable expression vector incorporating the cDNA of the invention which is under the suitable transcriptional control mechanisms, incorporating the vector into a eukayrotic or prokaryotic host organism and culturing the host organism and recovering polypeptide from the culture. These features and methods form a further aspect of the invention.

Also envisaged is the purification of chromatin/chromosome-bound structural proteins and catalytic factors such as Maturation Promoting Factor (MPF) in mitotic extracts which have been strongly implicated in chromatin/chromosome condensation.

When used in a therapeutic context, the polypeptides or factors described above may be combined with a pharmaceutical carrier or exipient. Hence pharmaceutical compositions form a further aspect of the invention.

The invention will now be particularly described by way of example with reference to the accompanying drawings in which:

The present invention is illustrated by way of following examples which should not be considered as limiting the scope of the invention.

EXAMPLE 1

Sperm Chromosome Dispersion or Decondensation

The HeLa interphase extracts (HIE) were prepared from cultures grown exponentially in suspension ($6-8\times10^6$ cells per ml, S3 type) as described for example by Banerjee and Cantor, Molecular and Cellular Biology, 10: 2863–2873, 1990; and Banerjee et al. Nucleic Acids Research 19: 5999–6006, 1991.

Human and pig sperm nuclei were prepared as follows: 5 ml of semen was liquefied by incubating at 37° C. for 45 min, and diluted to 50 ml by adding sperm wash buffer (SWB: 20 mM HEPES-KOH, pH 7.0, 100 mM potassium glutamate, 250 mM sucrose, 0.5 mM spermidine free base and 0.2 mM spermine tetrahydrochloride). After filtration through 8-layers of gauze, the diluted semen was spun at 2000 rpm for 15 min. The pellet was washed once with 50 ml of SWB, and resuspended in 2 ml of SWB. One ml of this suspension was gently layered over 4 ml of 70% per coll equilibrated with SWB and centrifuged at 3,000 rpm for 30 min. The sediment was carefully removed, washed twice with SWB, resuspended in 2 ml of SWB containing 0.05% lysolecithin (L-α-lysophosphotidylcholine) and incubated on ice for 10–12 min. The reaction was diluted by adding 3–4 volumes of cold SWB containing 3 mg/ml of BSA. The sperm were sedimented by centrifuging at 2000 rpm for 15 min. The pellet was washed twice with SWB containing BSA and finally with SWB alone. The permeabilized sperm were treated with 5 mM DTT for 15 min at room temperature. After pelleting again, the sperm were resuspended in SWB containing 1× protease inhibitor and 20% glycerol, counted using a haemocytometer, aliquoted, frozen in liquid nitrogen and stored at −70° C.

Lysolecithin permeabilized sperm nuclei were incubated at 35° C. in a 25–50μ reaction mixture containing 1000–5000 sperm per μl of HIE (18–22 μg of protein), 20 mM HEPES-KOH, pH 7.9; 150 mM KCl, 0.01 mM EDTA, 1× protease inhibitors, 1 mM DTT, 5 mM creatine phosphate (CP) and 1 mM ATP, either with or without 5 mM Mg++. To examine decondensation of the sperm nuclear chromatin, 4 ml of the reaction mixture was mixed with 4 ml of the buffer, containing 50% glycerol and 5 μg/ml of propidium iodide (PI), on a microscope slide and viewed using a fluorescence microscope (Nikon, Japan), equipped with phase rings and a photographic camera (FX-35DX). The phase and fluorescent micrographs were taken on either Kodak technical pan film (TP-135-36) or Fujichrome 400 D. The nuclear membrane was examined by mixing an aliquot of decondensed sperm with 10 μg/ml of DHCC (3,3'-Dihexyloxacarbocyanine Iodide, Kodak), dissolved in DMSO and subsequently in a buffer containing 50% glycerol and was viewed using a fluorescein filter (Nikon, B1 A).

Figure 1:
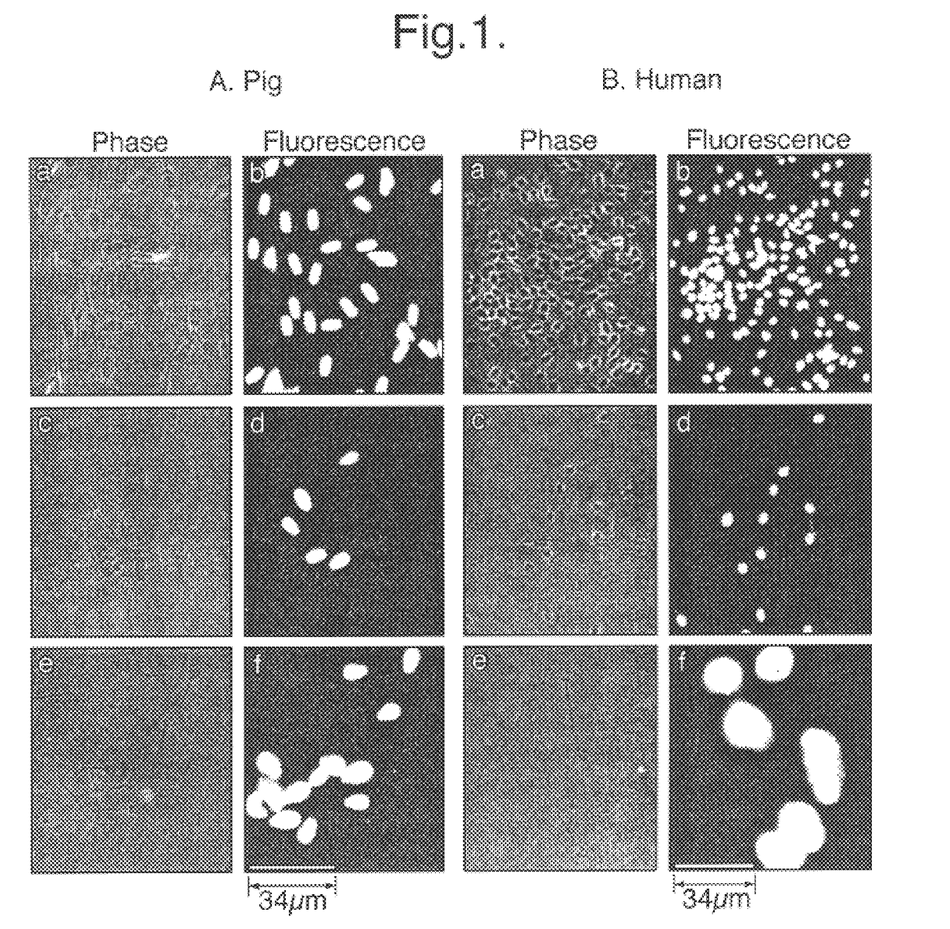
FIGS. 1A and 1B show the results of experiments with respect to the decondensation of sperm chromatin in HeLa extracts.
Figure 2:
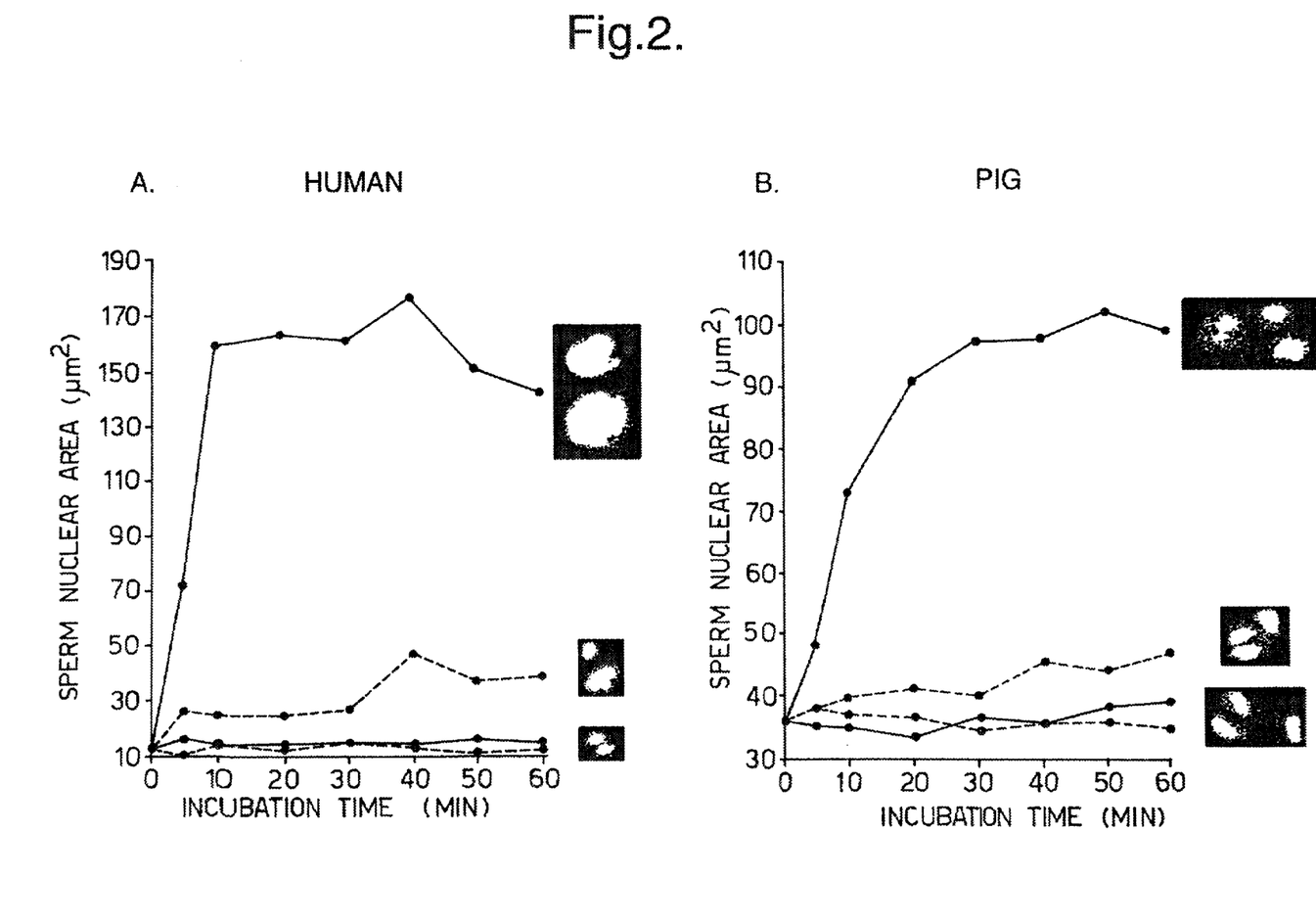
FIG. 2 shows in Part A and B graphically a time-course analysis of sperm chromatin decondensation.

The results are shown in FIGS. 1 and 2. The results shown in FIG. 1 can be broken down as follows: FIG. 1A (a & b), lysolecithin-treated pig sperm; c & d, sperm nuclei incubated in the buffer for 30 min at 35° C.; e & f, nuclei incubated in the extract for 15 min. FIG. 1B (a & b), lysolecithin-treated human sperm nuclei; c & d, nuclei incubated in the buffer for 30 min at 35° C.; e & f, nuclei incubated in the extract for 10 min. Bar: 34 μm.

FIG. 2 represents a time-course analysis of sperm chromatin decondensation. A & B, each time-point represents average area of 25–44 nuclear images captured randomly; closed circle (●), nuclei and extract; open circle (○), nuclei, extract plus 5 mM Mg++; closed triangle (▲), nuclei and buffer; open triangle (Δ), nuclei in buffer plus 5 mM Mg++. Right hand panels of each graph are examples of nuclear images processed for each conditions.

These results clearly show that the HeLa extract was highly efficient in effecting decondensation of sperm chromatin as evident by the rapid increase in sperm nuclear area.

EXAMPLE 2

Sperm Chromosome Condensation

The HeLa mitotic extracts (HME) were prepared as follows: cells were grown in suspension culture at a concentration of $5\times10^6$ cells per ml, and arrested at S-phase by adding an equal volume of fresh medium and thymidine at a final concentration of 2.5 mM. At 20 h, following thymidine addition, the cells were spun at 1000 rpm at room temperature for 5 min. The cells were washed twice with suspension culture medium (S-MEM) without serum to remove traces of thymidine. The washed cells were resuspended in a separate spinner flask using two-thirds of the original volume of complete medium. After 4–6 h of incubation, nocodazole, [5-(2-thienylcarbonyl)-1H-benzimidazole-2-yl] carbamate, was added at a concentration of 10 mg/ml. At 10 h following nocodazole addition 5 ml of the culture was aliquoted and the mitotic index determined by staining methanol-acetic acid fixed cells with Giemsa and observed using bright field microscopy.

Extracts were prepared only from cultures in which more than 90% cells were arrested at metaphase. The cells were sedimented by centrifuging at 1200 rpm for 5 min at 4° C. and washed three times in a buffer containing 20 mM HEPES pH 7.9, 80 mM b-blycerophosphate, 15 mM $MgCl_2$ and 20 mM EGTA. The pellet was resuspended in 4 volumes of the same buffer containing 1 mM γ-S ATP, 0.5 mM PMSF, 1× protease inhibitor cocktail (Leupeptin, chymostain, APMSF, pepstain A at 10 μg/ml; antipain and a protein in at 5 μg/ml), and homogenized on ice with 15 strokes in a teflon coated glass homogenizer. The homogenate was transferred to a flask containing 4 volumes of 50 mM Tris-HCl, pH7.9, 10 mM $MgCl_2$, 0.75M sucrose, 2 mM DTT and 50% glycerol. The mixture was gently stirred on ice for 5 min. Cellular proteins were extracted with saturated ammonium sulphate, pH 7.6, at a final concentration of 0.5M, for 30 min. The lysate was spun at 45,000 rpm for 3 h at 4° C. The clear supernatant was transferred to a flask held on ice and the proteins were precipitated with 0.33 g of ammonium sulphate per ml of the supernatant. The precipitated proteins were sedimented by centrifugation at 30,000 rpm for 30 min. The pellet was resuspended in a dialysis buffer (one-fifth the original volume of the supernatant) containing 20 mM HEPES-KOH, pH 7.9, 27 mM b-glycerophosphate, 150 mM potassium glutamate, 15 mM $MgCl_2$, 6.5 mM EGTA, 1 mM DTT, 0.1 mM γ-S ATP and 15% glycerol. Dialysis was carried out using one change of 30 volumes of the buffer for 8 h. The dialysed extract was clarified by centrifugation at 30,000 rpm for 30 min at 4° C. The clear supernatant was aliquoted, frozen in liquid nitrogen and stored at −70° C.

Sperm chromatin recondensation was carried out following two different protocols: a) the sperm chromatin was decondensed in the presence of 1 mM ATP, 5 mM creatine phosphate and 2.5 mM Mg++ in a 50 ml reaction for 1 h at 34° C. Twelve ml of mitotic extract and 250–400 μM γ-S ATP were added and further incubated for 90 min; b), the nuclei were first decondensed in the presence of ATP and creatine phosphate for 20 min, then 5 mM Mg++ was added and further incubated for 40 min before adding mitotic extract and γ-S ATP. Aliquots were stained with PI or DAPI (0.5 μg/ml), examined and photographed as described above.

Figure 3:
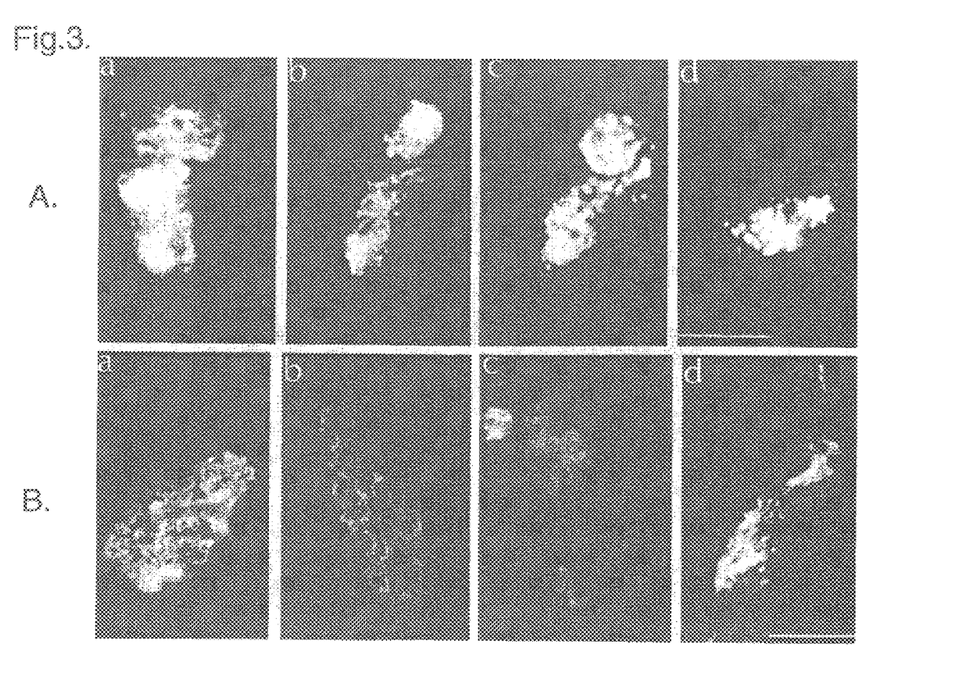
FIG. 3 shows in Part A and B the results of experiments with respect to the recondensation of sperm chromatin in HeLa mitotic extracts.

The results are shown in FIG. 3 which represents the following:

A, human sperm chromatin was dispersed in HME in the presence of 2.5 mM Mg++, 1 mM ATP and 5 mM CP for 20 min at 35° C., subsequently Mg++ was added to a final concentration of 5 mM before further incubation for 40 min. Incubation was continued for another 90 min in the presence of HME and γ-S ATP at 34° C.; B, same as A except no Mg++ was added during first 20 min of incubation; the data represent four different experiments in each set of conditions. Bar: A, 11.6 μm; B, 13.3 μm.

These results show the effectiveness of HME in sperm recondensation.

EXAMPLE 3

Purification of Sperm Chromatin Decondensation Factor

The HeLa extract described in Example 1 above was found to contain a cocktail of more than fifty different proteins. In order to obtain in isolated form the protein responsible for the sperm chromatin decondensation factor, a number of purification techniques were employed.

The purification experiment indicated that a group of high molecular weight proteins from phosphocellulose fractions may contain the critical factors, the most abundant of these being the 46 kDa component. However, further purification of this protein did not demonstrate the suspected activity and thus did not induce sperm chromatin condensation. The next abundant component, i.e. that having a molecular mass of 38 kDa was then purified. The same observation as regards the 46 kDa protein was made. Thus, the semi-purified 38 kDa protein did not induce decondensation of sperm chromatin. In the process of this study, it became clear that the decondensing factor is in fact present most abundantly in the flowthrough fraction of the phosphocellulose gradient, which now constituted a rich source of start material for further investigation.

An alternative technology was used to purify the rest of the selected components, since it turned out that the Mono Q chromatography system, which is generally accepted to be extremely potent for this type of protein separation, is nevertheless impractical for our particular purposes. The reason for this is that the system consistently became blocked by the proteins concerned. Using an alternative strong Anion Exchange Column (Q-Sepharose) the sperm chromatin decondensation factor was identified to being among a small number of protein fractions, among which one candidate of high molecular weight appeared to be mainly responsible for this action. However, this separation suffered from a problem of poor resolution.

Alternative protein purification protocols to the Q-Sepharose chromatographic technique to those mentioned above were developed. With the new protocols, the problem of poor resolution and identification of the sperm decondensing protein from Q-Sepharose fractions of SDS gels were overcome. Two resins namely, AG4×4 (Sigma), a weak anion-, and Resource Q (Pharmacia), a strong anion-exchange resins respectively, were used for the chromatographic purification of the protein. The purification protocols are shown schematically in FIG. 4.

Figure 4:
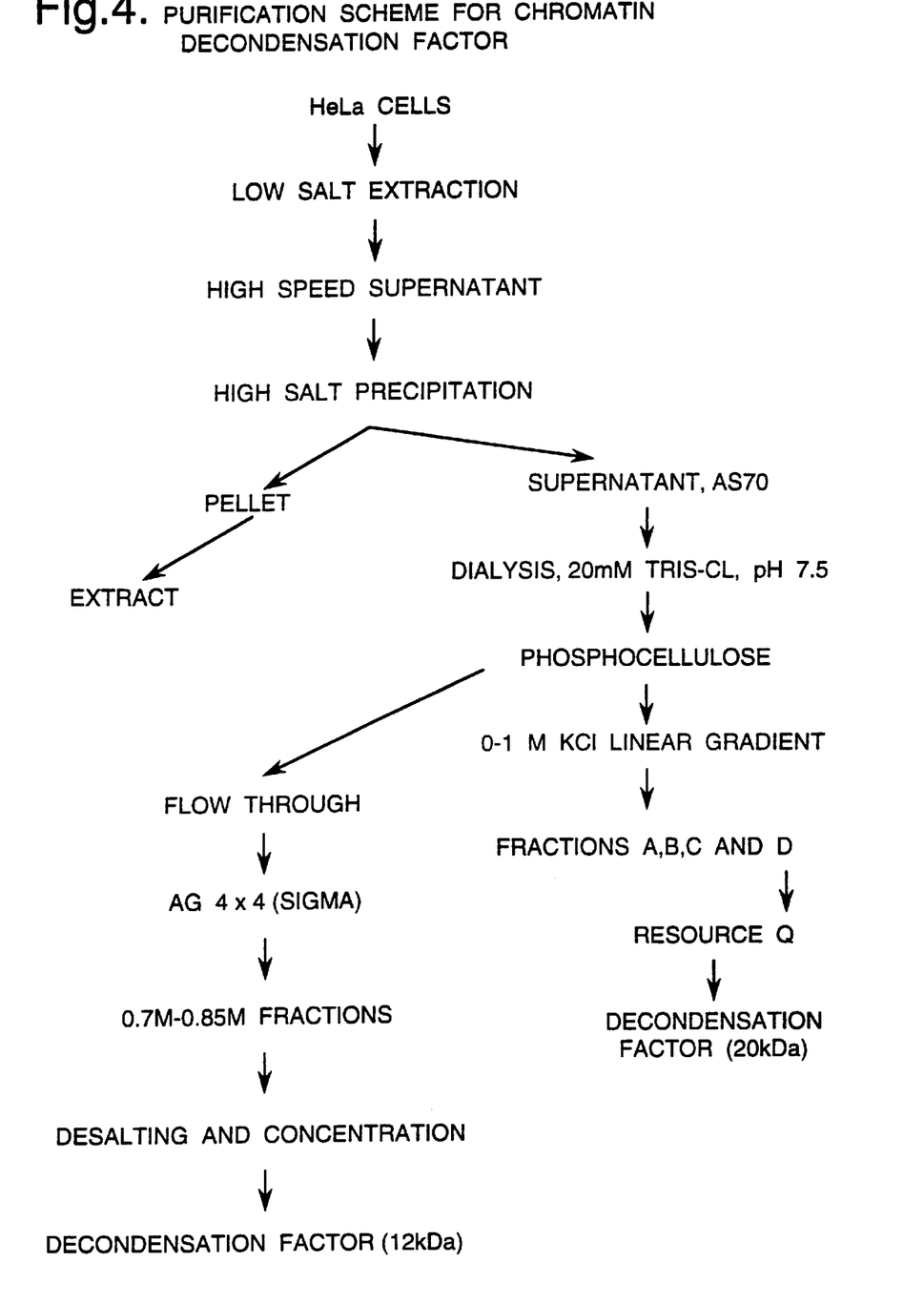
FIG. 4 illustrates a purification scheme for a decondensation factor.

The decondensing protein resolved on SDS gel with an approximate molecular mass of 20 kDa when fraction D from phosphocellulose (P-cel) chromatography was passed through Resource Q. However, when the P-cel flowthrough (P-cel-FT) fraction known to decondense the sperm nuclei, was passed through AG4×4, the sperm decondensing protein was restricted to the high salt fractions. The subsequent desalting and concentration of these fractions with Amicon centriprep resulted in the resolution of SDS gel of a protein with a smaller molecular mass of approximately 12 kDa. Although the structural identities or biochemical relationships, if any, of these two proteins have not been established it seems possible that the 12 kDa protein is a breakdown product of the 20 kDa protein.

EXAMPLE 4

ATP—Dependent Reorganisation of Human Sperm Nuclear Chromatin

Preparation of Sperm Nuclei

Purification of human sperm by sedimentation through Percoll and subsequent treatment with lysolecithin (L-α-lysophosphotidyl-choline) were as described in Example 1. The permeabilized sperm were resuspended in sperm wash buffer (SWE: 20 mM HEPES-NaOH, pH 7.0, 100 mM potassium glutamate, 250 mM sucrose, 0.5 mM spermidine free base and 0.2 mM spermine tetrahydrochloride) containing 1xprotease inhibitor cocktail (leupeptin, chymostain, APMSF, peptstain A at 10 μg/ml; antipain and aproteinin at 5 μg/ml), 50% glycerol and stored at −70° C.

Lysolecithin-permeabilized sperm nuclei were incubated at 35° C. for 1 hour in 250–300 μl reactions at concentrations of 2–3×10³ nuclei per μL in 20 mM HEPES-NaOH, pH 7.9, 150 mM KCl, 0.01 mM EDTA, 1 mM DTT, 5–6 mG $Mg^{2+}$, 1 mM ATP and 5 mM creatine phosphates (CP).

In order to determine whether the presence of exogenous cofactors is essential for protecting the nucleosome-length DNA fragments, the sperm nuclei were incubated in the presence or absence of ATP, $Mg^{2+}$ and creatine phosphate (CP). As controls, fresh nuclei or those incubated at 0° C. and 35° C. were also digested. Results from these experiments demonstrated that MNase digestion of sperm nuclei preincubated in the presence of ATP, $Mg^{2+}$ and CP resulted in the accumulation of DNA fragments (~190 bp) which comigrated with those of HeLA cells. Nuclease digestion of fresh sperm nuclei, or nuclei incubated at 0° C. or 35° C., produced smaller DNA fragments (147–155 bp), indicating that exogenous ATP and $Mg^{2+}$ altered the sperm chromatin structure such that Nu-DNA became less accessible to MNase compared to that of controls.

To further investigate the independent role of cofactors in sperm chromatin reorganization, nuclei were digested following incubation, either alone, in the presence of ATP and CP; in $Mg^{2+}$ alone, or in the presence of ATP, $M^{2+}$ and CP.

Results showed that sperm nuclei did contain some endogenous ATP and $Mg^{2+}$. Since exogenous $Mg^{2+}$ was sufficient for maximum accumulation of mononucleosome-length DNA fragments nuclei were subsequently incubated in the presence of $Mg^{2+}$ alone to maintain an identical specific activity of ATP in all reactions.

To examine whether ATP was hydrolysed during chromatin reorganisation, the endogenous ATP utilisation was competitively inhibited by incubating sperm nuclei in the presence of glucose and hexokinase (HK) prior to MNase digestion. Increasing concentrations of HK substantially reduced the yield of mononucleosomes (FIG. 2A). ATP-dependent reorganisation of sperm chromatin could be due to phosphorylation of chromosomal proteins, and nuclei were therefore treated with alkaline phosphatase following incubation with exogenous $Mg^{2+}$. Phosphatase treatment almost completely abolished the nucleosomal structure in reorganised chromatin, indicating that phosphorylation of chromosomal proteins is involved in chromatin rearrangements and maintaining stable nucleosomes.

What is claimed is:

1. A partially purified polypeptide obtainable from HeLa cells which is capable of effecting decondensation of chromatin or chromosomes and subsequently effecting the remodelling and recondensation of said chromatin or chromosomes.

2. A partially purified polypeptide according to claim 1 which is capable of effecting decondensation of sperm chromatin.

3. A partially purified polypeptide according to claim 1 or claim 2 obtainable from the interphase extract.

4. A partially purified polypeptide according to any one of claim 1 or claim 2 having a molecular weight of approximately 20 kDa.

5. A partially purified polypeptide according to any one of claims 1 or 2 having a molecular weight of approximately 12 kDa.

6. A process for preparing a partially purified polypeptide according to claims 1 or 2 which comprises culturing somatic cells, and isolating the polypeptide from cell extracts.

7. A process according to claim 6 wherein the extract is the supernatant fraction.

8. A partially purified polypeptide according to claims 1 or 2 for use in infertility diagnosis and/or treatment.

9. A partially purified polypeptide according to any one of claims 1 or 2 for use in contraception.

10. A polypeptide according to any one of claims 1 or 2 for use in the assistance of conception and/or the enhancement of natural conception.

11. A spermicidal agent comprising a polypeptide according to any one of claims 1 or 2 in combination with a carrier.

12. A contraceptive device which includes a spermicidal agent according to claim 11.

13. A pharmaceutical composition comprising a polypeptide according to any one of claims 1 or 2 in combination with a pharmaceutically acceptable carrier.

* * * * *